United States Patent [19]

Capizzi et al.

[11] Patent Number: 4,715,536

[45] Date of Patent: Dec. 29, 1987

[54] DISPENSER FOR THE SLOW RELEASE OF VOLATILE PRODUCTS

[75] Inventors: Amedeo Capizzi; Pia Spinelli, both of Milan; Emilio Arsura, San Donato Milanese, all of Italy

[73] Assignee: Montedison S.p.A., Milan, Italy

[21] Appl. No.: 900,262

[22] Filed: Aug. 26, 1986

Related U.S. Application Data

[63] Continuation of Ser. No. 751,854, Jul. 5, 1985, abandoned.

[30] Foreign Application Priority Data

Jul. 6, 1984 [IT] Italy .............................. 21783 A/84

[51] Int. Cl.4 ............................................... A61L 9/04
[52] U.S. Cl. ..................................................... 239/54
[58] Field of Search .................... 239/6, 34, 53–58, 239/60

[56] References Cited

U.S. PATENT DOCUMENTS

| | | | |
|---|---|---|---|
| 1,806,149 | 5/1931 | Daugherty | 239/57 |
| 3,578,545 | 5/1971 | Carson et al. | 239/53 |
| 3,790,081 | 2/1974 | Thornton et al. | 239/55 |
| 4,219,145 | 8/1980 | Jaeschke et al. | 239/60 |
| 4,320,873 | 5/1982 | Martens, III et al. | 239/6 |
| 4,445,641 | 5/1984 | Baker et al. | 239/6 |

*Primary Examiner*—Andres Kashnikow
*Assistant Examiner*—Mary Beth O. Jones
*Attorney, Agent, or Firm*—Stevens, Davis, Miller & Mosher

[57] ABSTRACT

Dispenser for the slow release of volatile pheromones comprising an adsorbing substrate of fibrils and/or fibers or their mixtures containing the active ingredient adsorbed or dispersed therein and coated with a layer which is impermeable to pheromones.

1 Claim, No Drawings

DISPENSER FOR THE SLOW RELEASE OF VOLATILE PRODUCTS

This application is a continuation of application Ser. No. 751,854 filed July 5, 1985, now abandoned.

The present invention concerns a dispenser for the slow release of volatile products.

More in particular the present invention concerns a dispenser having the characteristic of releasing volatile products at a slow, pre-determined and controlled speed.

The words volatile products, as used in the present description and in the claims, mean all those compounds which are active in the air. Examples of such products are odorous essences, deodorants, disinfectants, attractants for insects, such as pheromones or formulations containing one or more pheromones; insecticides with abating, asphyxiating, fumigant, repellent, etc. activity or combinations of same.

As it is known, these products in order to develop their activity need to be released totally and in a controlled and constant way for a more or less prolonged time with respect to desired persistence.

Systems known which allow one to obtain a slow release of these products are: solutions of high boiling liquids used as such or absorbed on different supports; non-porous simple or multi-layer polymeric systems incorporating the active ingredient; microcapsules with walls in polyamide (U.S. Pat. No. 3,577,515 or in gel (U.S. Pat. Nos. 2,800,457 and 2,800,458) containing the active ingredient; hollow fibres consisting of capillaries having one of their ends open from which the active ingredient volatilizes (U.S. Pat. No. 4,017,030).

These systems, however, are in practice not completely satisfactory in that they generally require particular attention both for their preparation and above all for their subsequent distribution in the ambient to be treated. Moreover, in these known systems the kinetics of release of the active ingredient is not linear in that it depends on the amount of product remaining in the system, on the chemical composition of the formulation components, on ambient factors such as light, temperature, humidity, wind and the like.

Another drawback of the known systems lies in the fact that they do not allow one to adjust and regulate the speed at which the active ingredient is released and furthermore part of the latter remains adsorbed by the system itself.

The object of the present invention is to provide a dispenser capable of releasing to the air a volatile product in a regular, total and reproducible way, at predeterminable and adjustable speed according to the different volatility of the products and different ambient conditions.

It has now been discovered that this object and others are obtained by means of a dispenser comprising a substrate of natural, artificial or synthetic fibres and/or fibrils or their mixtures, containing the active ingredient adsorbed or dispersed and coated by a layer impermeable to gases and vapours provided with openings.

The coating layer can be a film of aluminium, nylon, polyester, polyvinylchloride, a polyolefin such as polypropylene, polyethylene, ethylene-propylene copolymers, etc. alone or combined with each other or with other films in order to provide them with the desired properties and hot weldability. Examples of films suitable for being used for the coating of the fibrous substrate are multi-layer films consisting of polyethylene-polyester, polyethylene-aluminum-polyester, polyethylene-nylon-polyester, or of polyethylene-aluminium-paper.

The dispenser of the present invention can have any shape or size according to the needs and the situations in which it is used. Thus, for instance, it can be a parallelepiped with square, rectangular or in general polygonal section or else a cylinder or a sphere, etc.

The openings provided in the dispenser can be represented by the side faces of the parallelepiped, by one or both the bases of the cylinder or by slots or holes provided on the dispenser surface.

The dispenser of the present invention can be provided with notches ending in through holes which have the function of both fixing the dispenser itself and releasing the active product.

The dispenser of the present invention can also be obtained by means of a layer of adhesive applied onto its impermeable surface.

Any natural, synthetic and artificial fibre or fibril can be used to form the substrate. In practice fibres or fibrils which can be hot welded to the impermeable layer are preferred.

So for example polyethylene fibrils are particularly preferred for their property of being easily hot welded to the multi-layer films containing polyethylene as surface layer.

Cellulose fibres, alone or in combination with polyethylene fibrils, can be used as well.

The fibrous substrate can be paper, fabric, non-fabric, felt, etc.

The dispenser of the present invention can be prepared by making the fibrous substrate stick to the impermeable layer and then soaking the manufactured article with a solution of the active ingredient, or else by dispersing the active ingredient as such or in mixture in the fibrous substrate and making the impermeable layer adhere to it. The adhesion of the substrate to the coating can be obtained by hot welding, gluing, adhesion, etc. In the event of hot welding, temperature and pressure are regulated according to the fibrous material used, in order to avoid melting of said fibrous material and to maintain the desired porosity.

Temperatures ranging between 80° and 250° C. and pressures ranging between 0.5 and 5 Atm can be used.

In the dispenser of the present invention, the speed of release of the active ingredient depends both on the free surface through which the product comes in contact with the air and on the possibility of internal migration of the product itself. Therefore by appropriately regulating the size of the openings and the density of the substrate it is possible to adjust the release speed at the desired value.

The duration of activity of the dispenser according to the present invention depends on the release speed and on the amount of the active ingredient contained in the free volume inside the fibrous substrate.

In order to better illustrate the present invention and to put it into practice, some illustrative exemplifying but not limiting examples are given hereunder.

EXAMPLE 1

Paper having 1.25 mm thickness consisting of polyethylene fibrils (FERLOSA-registered trade-mark) was coated on the two faces, at 115° C. and in a mould having 1 mm thickness, with a three-layer film of polyester-aluminium-polyethylene being 15 micron, 8 micron and 90 micron thick respectively, placed in such a way that the polyethylene layer is turned towards the paper.

Subsequently the coated paper was cut into squares having 20 mm in side.

Each square was soaked by capillarity with 100 mg of tetradecenyl acetate, a product having approximately the same volatility as the sexual pheromones of many species of lepidocters (sample 1).

Analogously equal squares (sample 2) derived from the Ferlosa paper alone were soaked.

Five squares of each type were placed in any airy room (speed of the air: 1.5 mt/sec approx.) at a constant temperature of 25° C. At different times samples were taken and the amount of remaining tetradecenyl acetate was determined by gas chromatographic analysis. Data are reported in the following Table 1:

TABLE 1

| DAYS | mg of TETRADECENYL ACETATE REMAINED | |
|---|---|---|
| | SAMPLE 1 | SAMPLE 2 |
| 4 | 95 | 40 |
| 8 | 88 | 5 |
| 16 | 79 | 0 |
| 32 | 60 | 0 |
| 64 | 26 | 0 |

EXAMPLE 2

A paper 1.10 mm in thickness containing 80% of polyethylenic fibrils (Ferlosa) and 20% of cellulose (380 g/sq.mt) was coupled, at 115° C., on both surfaces with a film such as the one used in the example 1. From the resulting product, 0.80 mm thick, disks of 15 mm in diameter were drawn and said disks were immersed into a dichloro-methane solution containing the pheromones mixture of *Cacoecimorpha pronubana* (B E G A of the carnation) in a concentration corresponding to 10% by weight, 3% by weight of 2-hydroxy-4'-octyloxy-benzophenone (stabilizer) and 3% by weight of 2,6-di-ter-butyl-phenol propionate of pentaerythrite (anti-oxidizer).

Each disk, after evaporation of the solvent, contained approximately 4.5 mg of cis-11-tetradecenyl acetate, 0.25 mg of cis-11-tetradecenol, 0.25 mg of cis-9-tetradecenol and 5 mg of tetradecenyl acetate together with 1 mg of stabilizer and anti-oxidizer respectively.

The dispensers so soaked were placed into traps Mastrap ® (sample 3) in comparison with identical traps (sample 4) fitted with rubber capsules containing the same substances. The results obtained (see Table II hereunder) proved a significant difference both in the total number of captures and in the persistence of the attractive activity with best performance of sample 3.

TABLE II

| EXPOSURE PERIOD | NUMBER OF CAPTURES | |
|---|---|---|
| IN DAYS | SAMPLE 3 | SAMPLE 4 |
| From 0 to 7 | 28 | 24 |
| From 7 to 14 | 75 | 32 |
| From 14 to 21 | 92 | 19 |
| From 21 to 28 | 58 | 22 |
| From 28 to 35 | 48 | 11 |
| From 35 to 42 | 31 | 7 |
| From 42 to 49 | 27 | 3 |

EXAMPLE 3

Operating according to the procedure described in example 2, squares having 20 mm in side and 0.75 mm in thickness were prepared, their fibrous substrate being constituted by paper comprising 60% by weight of Ferlosa and 40% by weight of cellulose and having a thickness of 1.10 mm and a weight of 390 g/cu.mt. Said squares were soaked with 5 mg of cis-5-dodecenyl acetate and 1 mg of stabilizer and anti-oxidizer respectively of the example 5.

Analogously, using paper having 200 g/sq.mt. in weight and consisting of 60% by weight of Ferlosa and 40% by weight of cellulosa, squares having 20 mm in side and 0.45 mm in thickness were prepared. Said squares were soaked with 5 mg of cis-3-decenylacetate and 1 mg of stabilizer and antioxidizer respectively of the example 2. Cis-5-dodecenylacetate and cis-3-decenylacetate are components of the sexual pheromones of the Lepidocter *Cossus cossus*.

A square containing cis-5-dodecenylacetate and one containing cis-3-decenyl acetate were clinched together and suspended in a trap with equilateral triangular prism shape (prism height: 40 cm, triangle side: 20 cm) with two openings instead of the triangular faces; the horizontally placed one of the three internal walls is covered with glue.

Another identical trap was fitted with two rubber dispensers each containing the same amounts of cis-5-dodecenyl acetate and cis-3-decenyl acetate.

The traps were suspended in a willow and poplar wood at Monticelli Pavese (PV). The results expressed as number of males of *Cossus cossus* species captured are reported in the following Table III; the test was carried out in a period from June 15 to July 19, 1983.

TABLE III

| PERIOD OF EXPOSURE IN DAYS | RUBBER CAPSULE | SQUARES |
|---|---|---|
| From 0 to 7 | 8 | 9 |
| From 7 to 14 | 3 | 11 |
| From 14 to 21 | 1 | 17 |
| From 21 to 28 | 0 | 8 |
| From 28 to 35 | 0 | 5 |

EXAMPLE 4

A paper of the type described in the example 2 was coated at 115° C. with the film of the example 1 on the two faces. The resulting product had a thickness of 0.75 mm.

Squares of 20 mm in side were prepared and imbued according to the procedure of the example 2 with a solution consisting of:

cis-8-dodecenyl acetate: 36.2%
trans-8-dodecenyl acetate: 2.7%
cis-8-dodecenol: 2 0.3%
UV stabilized of ex. 2: 0.4%
anti-oxidizer of ex. 2: 0.4%
dichloro-methane: 60%

After evaporation of the solvent, each square contained approximately 20 mg of the pheromonic mixture attractive for the males of *Cydia molesta* species (Cidia of the peach-tree) and approximately 1 ml. of stabilizer and anti-oxidizer respectively.

The squares were applied by clinching to the peach-tree branches of a plot of 2,000 sq.mt. at Volpedo (AL), one for each tree. The dose of pheromones applied was equal to 10 g/ha.

A commercial trap Traptest ® for the assessment of the *Cydia molesta* population was placed at the centre of the plot, while a similar trap was placed at the centre of a similar peach grove approximately 200 mt far from the first one.

The test of confusion was carried out during the months of May and June. Only 3 captured insects were found during the last week of June in the trap placed in the plot where the squares containing pheromones were placed, while in the trap placed in the peach grove there was a total number of 793 captured insects, thus proving an almost complete confusion of the males of *Cydia molesta*.

EXAMPLE 5

A paper having 0.55 mm in thickness containing 40% of cellulosa and 60% of polyethylene fibrils (Ferlosa) (weighing 200 g/sq.mt.) was coated at 115° C. on both faces with two three-layer films as mentioned in the example 1. The resulting product, having 0.45 mm in thickness, was cut into squares of 22 mm in side and each of them was provided with a hole having a diameter of 3 mm and with a cut extending from said hole up to one of the sides of the square itself.

The squares were imbued by immersion into a solution having the following composition:

cis-11-tetradecenyl acetate: 13.4%
cis-9-tetradecenyl acetate: 3.4%
cis-11-tetradecenol: 1.6%
cis-9-tetradecenol: 1.6%
UV stabilizer of ex. 2: 4.0%
anti-oxidizer of ex. 2: 4.0%
dichloro-methane: 72.0%

After the evaporation of the solvent, each square contains approximately 5 mg of the aforesaid pheromonic mixture attractive for *Epichoristodes acerbella* (South-African TORTRICE of the carnation) and approximately 2 mg of stabilizer and anti-oxidizer.

The squares were applied to the supporting wires of a carnation grove of approx. 5000 sq.mt., one square every 5 sq.mt. The dose of pheromones applied was equal to 10 g/ha.

The test of confusion was carried out at Ospedaletti (IM)-Italy and was surveyed by controlling the insects captured in three commercial traps Traptest ® placed in said plot compared with three similar traps placed in a similar adjacent grove and by evaluating damages by sampling sprouts and buds taking root in both grooves.

The test was carried out from the month of April to the month of September; 3 applications of the above-mentioned dispensers were performed during this period.

During the six months of test, in the traps placed inside the area where the pherohormone dispensers were distributed, no capture of *Epichoristodes acerbella* was reported, while in the traps placed in the control plot, a total of 396 males were captured.

The percentage of sprouts and buds damaged was equal to 0.9% in the area where the dispensers had been placed and to 5.5% in the control plot submitted to the usual treatments with conventional insecticides.

EXAMPLE 6

A paper 0.55 mm in thickness consisting of 60% of FERLOSA and 40% of cellulose, weighing 200 g/sq.mt was coated at 115° C. on both faces with a three-layer film of polythene-nylon-polythene having thickness of 35 micron, 25 micron and 95 micron respectively.

The thickness of the coated product was 0.46 mm.

It was then cut into small squares 7 mm on a which were soaked by immersion into a dichloro-methane solution of trans-9-dodecenyl acetate (sexual pheromones of the Lepidocter *Loxostage verticalis*), of the stabilizer and the antioxidizer of the example 2.

After the evaporation of the solvent, each square contained approximately 500 μg of trans-9-dodecenyl acetate and approximately 250 μg of stabilizer and antioxidizer.

A lucern-field of approximately 5000 sq.mt placed at Volpedo (AL) was treated with 10,000 of these small squares which were distributed manually.

At the moment of the treatment the small squares were immersed into an emulsion of a particular adhesive based on polymers of butene and polyisobutene so as to make them stick to the small plants.

The test was carried out by controlling the males of the *Laxostege verticalis* captured in a commercial trap Traptest ® placed at the centre of said lucern-field comparing the result with the one obtained in a similar trap placed at the centre of a similar field placed 400 mt from the first one.

During the test the trap placed in the plot where the pheromones dispensers had been distributed captured only 4 males of *Loxostege verticalis* in the last week of August, while the one placed in the control field caught a total of 131 insects.

We claim:
1. A multilayer dispenser, provided with openings, having a size of 2 cm on a side and a thickness ranging between 0.4 and 2 mm, for the slow release of volatile pheromones comprising an adsorbing substrate consisting of polyethylene fibrils alone or combined with cellulose fibers containing the active ingredient adsorbed or dispersed therein and coated on the two faces with a multi-layer polyester-aluminum-polyethylene film which is impermeable to pheromones and in which the polyethylene layer is hot-welded to the substrate.

* * * * *